United States Patent [19] [11] 4,078,086
Winkelmann et al. [45] Mar. 7, 1978

[54] ANTHRAQUINONE-BIS-AMIDINES AND PROCESS FOR PREPARING THEM

[75] Inventors: Erhardt Winkelmann, Kelkeim, Taunus; Wolfgang Raether, Dreieichenhain, both of Germany

[73] Assignee: Hoechst Aktiengesellschaft, Frankfurt am Main, Germany

[21] Appl. No.: 685,792

[22] Filed: May 12, 1976

[30] Foreign Application Priority Data

May 14, 1975  Germany ............................ 2521357

[51] Int. Cl.² ................... A61K 31/155; C07C 123/00
[52] U.S. Cl. ................................ 424/326; 260/239 B; 260/293.62; 260/564 R; 542/415; 424/244; 424/267; 424/274
[58] Field of Search .......................... 260/378, 564 R; 424/326

[56] References Cited
U.S. PATENT DOCUMENTS
3,184,482  5/1965  Steiger .................................. 260/378

Primary Examiner—Gerald A. Schwartz
Attorney, Agent, or Firm—Curtis, Morris & Safford

[57] ABSTRACT

Novel compounds of anthraquinone-bis-amidines are prepared which are suitable for combating diseases caused by trichomonads.

7 Claims, No Drawings

ANTHRAQUINONE-BIS-AMIDINES AND PROCESS FOR PREPARING THEM

The present invention relates to anthraquinone-bis-amidines of the formula I

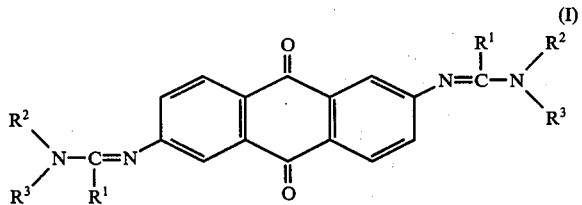

wherein $R^1$, $R^2$, $R^3$ may be identical or different and may represent hydrogen, straight-chained or branched alkyl having 1 to 4 carbon atoms, such as methyl, ethyl, propyl, isopropyl, butyl or isobutyl and wherein $R^1$ and $R^2$ as alkylene chain having 3 to 5 carbon atoms are together with the nitrogen and hydrocarbon atom of the amidino group constituent of a pyrrolidine, piperidine or hexamethylene-imine ring, or wherein $R^2$ and $R^3$ as alkylene chain having 4 to 5 carbon atoms may represent together with the nitrogen atom of the amidino group constituent of a pyrrolidine, piperidine, morpholine or thiomorpholine ring as well as the addition salts of these compounds (I) with a physiologically compatible acid.

The invention further relates to a process for preparing anthraquinone-bis-amidines of the formula I as well as of the addition salts thereof with a physiologically compatible acid, which comprises A. reacting 2,6-diamino-anthraquinone of the formula II

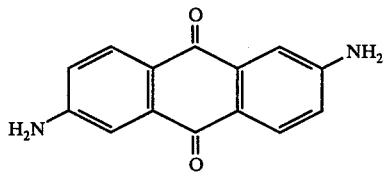

a. with a carboxylic acid amide, carboxylic acid thioamide, lactame or thiolactame of the formula III

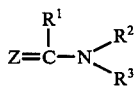

wherein Z is oxygen or sulfur and $R^1$, $R^2$ and $R^3$ have the above meaning, in the presence of a condensation agent, or b. reacting with an acetal of a carboxylic acid amide or a lactam of the formula IV

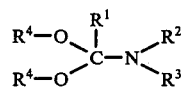

wherein $R^1$, $R^2$, $R^3$ have the above meanings and $R^4$ represents methyl or ethyl, or B. reacting a bis-trihalogenoethylidene compound of the formula V

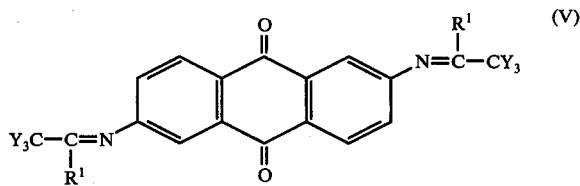

wherein $R^1$ has the above meaning and Y is halogen, especially fluorine, chlorine, bromine, with an amine of the formula VI

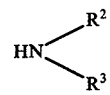

wherein $R^2$ and $R^3$ have the above meanings, or

C. reacting a bis-iminochloride compound of the 2,6-diaminoanthraquinone of the formula VII

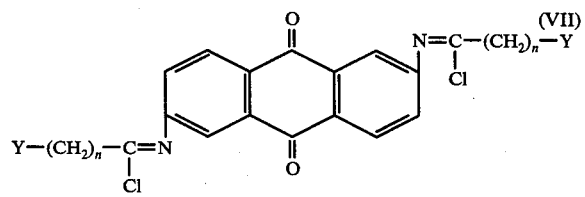

wherein Y is halogen, especially fluorine, chlorine or bromine, and n is the number 3, 4 or 5, with an amine of the formula VIII $$H_2N - R^3 \qquad \text{VIII}$$

wherein $R^3$ has the above meaning, or

D. reacting a bis-isocyanate of the formula IX

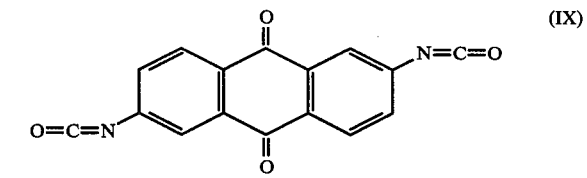

with a compound of the formula III, or

E. reacting a bis-carbamic acid chloride of the formula X

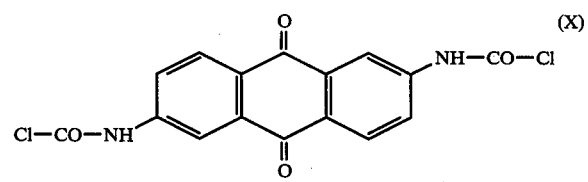

with a compound of the formula III.

As starting materials of the formula III (carboxylic acid am des and thioamides) there may be used for example formamide, thio-formamide, N-methyl-, N-ethyl-, N-propyl-, N-isopropyl-, N-butyl-, N-isobutyl-, N,N-dimethyl-, N,N-diethyl-, N,N-dipropyl-, N,N-diisopropyl-, N,N-dibutyl-, and N,N-diisobutyl-formamide, as well as the corresponding derivatives of thio-oformamide, acetamide, thioacetamide, propionamide, thiopropionamide, butyramide, thiobutyramide, valeramide, thiovaleramide, moreover, N-formyl, N-acetyl, N-propionyl, N-butyryl and N-valeryl compounds of pyrrolidine, piperidine, morpholine and thiomorpholine.

Further starting materials of the formula III (lactams and thiolactames) are for example butyrolactam (pyrrolidone-2), caprolactam (piperidone-2), caprolactame (2-oxohexamethylene-imine), butyro-, valero-, or capro-thiolactam, N-methyl-, N-ethyl-, N-propyl-, N-butyl derivatives of butyro-, valero- and capro-lactame and of butyro-, valero-, and capro-thiolactam.

Starting materials of the formula IV are for example formamide and its homologues, N-methyl-, N-ethyl-, N-propyl-, N-isopropyl-, N-butyl-, N-isobutyl-, N,N-dimethyl-, N,N-diethyl-, N,N-dipropyl-, N,N-diisopropyl-, N,N-dibutyl- and N,N-diisobutyl-formamide, as well as the corresponding derivatives of acetamide, propionamide, butyramide or valeramide the corresponding acetals of the above-mentioned amides, especially -dimethyl-diethyl-acetal, furthermore N-formyl-, N-acetyl-, N-propionyl-, N-butyryl-, N-valeryl-pyrrolidine, -piperidine, -morpholine, -thiomorpholine, the corresponding acetals of the above-mentioned amides, especially dimethyl or diethylacetal, furthermore butyrolactam (pyrrolidon-2), valerolactam (piperidone-2), caprolactam (2-oxohexamethylene-imine), butyro-, valero-, capro-thiolactam, N-methyl-, N-ethyl-, N-propyl-, N-butyl-butyro-lactam, -valero-lactam, -caprolactame, -butyro-, valero-, -capro-thiolactam, as well as the corresponding acetals of the above-mentioned lactams, especially dimethyl or diethylacetal.

Starting materials of the formula V are for example 2,6-bis-trifluoro- (chloro, bromo)-ethylidene-imino-anthraquinone, 2,6-bis-trifluoro-(chloro, bromo)-propylidene-imino-anthraquinone, 2,6-bis-trifluoro-(chloro, bromo)-butylidene-iminoanthraquinone,.

Starting materials of the formula VI are for example ammonia, alkyl-amines such as methyl-, ethyl-, propyl-, isopropyl-, butyl-, isobutyl-, dimethyl-, diethyl-, dipropyl-, diisopropyl-, dibutyl-, diisobutyl-amine as well as cyclic amines such as pyrrolidine, piperidine, morpholine, thiomorpholine.

Starting materials of the formula VII are for example anthraquinone-2,6-bis-ω-chloro-(bromo)-butyro-, -valero-, or -capro-imidochloride.

Starting materials of the formula VIII are for example ammonia, methyl-, ethyl-, propyl-, isopropyl-, butyl-, isobutyl-amine.

The starting materials of the formula II, III, IV, VI and VIII are known in literature.

The starting materials of the formula V may be prepared by reacting 2,6-diamino-anthraquinone with trifluoro-(chloro-bromo)-acetaldehyde (fluoral, chloral, bromal) or with 1,1,1-trifluoro-(chloro-bromo)-acetone at elevated temperature with splitting of water.

The starting materials of the formula VII may be prepared by reacting 2,6-diamino-anthraquinone with ω-halogenalkanoic acid chlorides, such as ω-chlorobutyric acid chloride, ω-chloro-valeric acid chloride, ω-chloro-caproic acid chloride to the corresponding amides and subsequently converting them into the imide chlorides with phosphorpentachloride.

The starting materials of the formula IX and X may be prepared in known manner by reacting 2,6-diamino-anthraquinone with phosgene; thus, the compounds X are formed at low temperature, the compounds IX at temperatures above 100° C.

The reactions according to the variants (A) to (E) of the process of preparation are expediently carried out in equivalent amounts of the corresponding starting materials. In the case of volatile reactants it is recommended to use an excess.

The reactions are preferably carried out in a solvent or distributing agent, but certain reactions may also be carried out without solvent or distributing agent, as it can be seen below:

As solvents or distributing agents there are considered for example: In the process (A)(a) aromatic, if desired halogenated hydrocarbons, such as benzene, toluene, xylene, chlorobenzene, dichlorobenzene, trichlorobenzene; chlorinated aliphatic hydrocarbons such as methylene chloride, chloroform; aliphatic ethers such as di-isopropyl ether, ethyleneglycol dimethyl ether, -diethyl ether, diethylene-glycol-dimethyl ether, tetrahydrofurane, dioxane.

It is particularly advantageous to use in excess the carboxylic acid amides or lactams of the formula III used for the reaction. If desired, the excess may be recovered when working up the reaction batch.

In the process (A)(b) alcohols such as methanol, ethanol, propanol, butanol, methoxyethanol, ethoxyethanol or preferably the acetals of the carboxylic acid amides or lactams of the formula IV used for the reaction are used in excess.

In the process (B) to (E) higher boiling, aromatic, if desired, halogenated hydrocarbons such as toluene, xylene, monodi-, trichlorobenzene, nitrobenzene are used; the reaction is preferably carried out without solvent or with an excess of the reactants of the formula VI in the process (B), of the formula VIII in the process (C), of the formula III in the process (D) or (E).

The reactants according to process (A)(a) are preferably carried out in the presence of a condensing agent. As condensing agents there may preferably be mentioned organic and inorganic acid halides, for example thionyl chloride, phosphorotrichloride, phosphoropentachloride, phosphoroxy chloride, chlorosulfonic acid, phosgene, oxalyl chloride, chloroformic acid alkyl esters, benzoyl chloride, benzenesulfo acid chloride, 4-toluene-sulfo acid chloride.

If in the reaction according to process (A)(a) carboxylic acid thioamides or thio-lactams are used in simultaneous use of a sulfur-binding agent is recommended. Such agents are for example heavy metal oxides such as mercury oxide and lead oxide.

The reaction components according to process (A)(a) are expediently reacted in equivalent amounts, i.e. per 1 mol of 2,6-diamino-anthraquinone 2 mols of carboxylic acid amide, or -thioamide, lactam, thiolactam and 2 mols of acid halide, as well as 2 mols of sulfur-binding agent, if desired. The three last-mentioned components, especially the carboxylic acid amides and lactams may be preferably used in excess (as solvent).

Depending on the variant of the process the reaction temperatures are between 0° and 200° C, preferably in the process (A)(a) and (A)(b) between 25° and 100° C,
process (B) and (C) between 80° and 120° C,
process (D) and (E) between 150° and 180° C.

Depending on the variant of the process and on the temperature range the reaction times are between several minutes to some hours.

The reaction products according to (A)(a) are obtained in the form of their salts. They may be isolates as such or, if desired, converted into the free bases by adjusting the aqueous solutions to an alkaline range.

For adjusting to an alkaline range usually strong bases are used, such as ammonia, sodium carbonate, potash, caustic soda, caustic potash or the aqueous solutions thereof. The bases set free may be converted into salts with physiologically compatible acids.

Physiologically tolerable acids are for example halogen hydracids, especially hydrochloric acid, furthermore sulfuric acid, phosphoric acid, acetic acid, propionic acid, lactic acid, tartaric acid.

If required, a purification fo the products of the process may take place by recrystallization from a suitable solvent or solvent mixture.

The novel compounds of formula I are well compatible and are suitable for combating protozoal diseases in human beings and animals, as they are caused for example by infections with *Entamoeba histolytica.* They also act against trichomonades such as *Trichomonas foetus.*

The compounds are administered orally in the form of pharmaceutically usual preparations, for example as tablets or capsules, which contain per dosage unit from about 5 to 750 mg of the active ingredient in admixture with a usual carrier and/or constituent.

Depending on each individual case, the individual dose administered to the patient ranges from 2 to 100 mg of active ingredient per kilogram of body weight.

The following Examples illustrate the invention.

EXAMPLE 1 : (Method A/a)

(1.1)
2,6-Bis-(dimethylamino-methylene-imino)-anthraquinone 238 g (1 mol) of 2,6-diamino-anthraquinone were suspended in 2.5 l of dimethylformamide and, at 30°–40° C, 310 g (2 mols) of phosphoroxy chloride were added dropwise, while stirring. Then the mixture was heated with stirring to 75° C. When cooling the final product began precipitating as a salt. By addition of methylene chloride or acetone the crystallization could be completed. The salt was suction-filtered, washed with methylene chloride, suction-filtered until dry, dissolved in 700 ml of water, alkalinized with aqueous concentrated ammonia, and the free base was extracted several times with methylene chloride or chloroform. The combined organic extracts were dried with sodium sulfate, evaporated and the residue was recrystallized from dimethylformamide.

Thus, 275 g ( 79% of the theocetical yield) of 2,6-bis-(dimethylamino-methylene-imino)-anthraquinone were obtained in the form of orange crystals having a melting point of 237° C.

From the free base the dihydrochloride (melting point > 300° C) could be prepared in usual manner with molar amounts of alcoholic hydrochloric acid.

According to the process described in Example 1 the following compounds were obtained:

(1.2) From the 2,6-diamino-anthraquinone (DAQ) and formamide the 2,6-bis-(amino-methylene-amino)-anthraquinone.
(1.3) From DAQ and N-methylformamide the 2,6-bis-(methylamino-methylene-imino)-anthraquinone.
(1.4) From DAQ and N-ethyl formamide the 2,6-bis-(ethylamino-methylene-imino)-anthraquinone.
(1.5) From DAQ and N-n-propylformamide the 2,6-bis-(n-propylamino-methylene-imino)-anthraquinone.
(1.6) From DAQ and N-isopropylformamide the 2,6-bis-(isopropylamino-methylene-imino)-anthraquinone.
(1.7) From DAQ and N-n-butylformamide the 2,6-bis(n-butylamino-methylene-imino)-anthraquinone.
(1.8) From DAQ and N-isobutylformamide the 2,6-bis-(isobutylamino-methylene-imino)-anthraquinone.
(1.9) From DAQ and N-diethylformamide the 2,6-bis-(diethylamino-methylene-imino)-anthraquinone having a melting point of 173° C.
(1.10) From DAQ and N-di-n-propylformamide the 2,6-bis-(di-n-propyl-methylene-imono)-anthraquinone having a melting point of 173° C.
(1.11) From DAQ and N-diisopropylformamide the 2,6-bis-(diisopropylamino-methylene-imino)-anthraquinone.
(1.12) From DAQ and N-di-n-butylformamide the 2,6-bis-(di-n-butylamino-methylene-imino)-anthraquinone having a melting point of 50° C.
(1.13) From DAQ and N-diisobutylformamide the 2,6-bis-(diisobutylamino-methylene-imino)-anthraquine.
(1.14) From DAQ and N-formylpyrrolidine the 2,6-bis-(pyrrolidino-methylene-imino)-anthraquinone having a melting point of 293° C.
(1.15) From DAQ and N-formylpiperidine the 2,6-bis-(piperidino-methylene-imino)-anthraquinone having a melting point of 300° C.
(1.16) From DAQ and N-formylmorpholine the 2,6-bis-(morpholino-methylene-imino)-anthraquinone having a melting point of 300° C.
(1.17) From DAQ and N-formylthio-morpholine the 2,6-bis-(thiomorpholino-methylene-imino)-anthraquinone having a melting point of 275° C.
(1.18) From 2,6-diamino-anthraquinone (DAQ) and acetamide the 2,6-bis-(amino-1-ethylene-imino)-anthraquinone.
(1.19) From DAQ and N-methylacetamide the 2,6-bis-(methylamino-1-ethylene-imino)-anthraquinone.
(1.20) From DAQ and N-ethylacetamide the 2,6-bis-(ethylamino-1-ethylene-imino)-anthraquinone.
(1.21) From DAQ and N-n-propylacetamide the 2,6-bis-(n-propylamino-1-ethylene-imino)-anthraquinone.
(1.22) From DAQ and N-isopropylacetamide the 2,6-bis-(isopropylamino-1-ethylene-imino)-anthraquinone.
(1.23) From DAQ and N-n-butylacetamide the 2,6-bis-(n-butylamino-1-ethylene-imino)-anthraquinone.
(1.24) From DAQ and N-isobutylacetamide the 2,6-bis-(isobutylamino-1-ethylene-imino)-anthraquinone.
(1.25) From DAQ and N-dimethylacetamide the 2,6-bis-(dimethylamino-1-ethylene-imino)-anthraquinone having a melting point of 306° C.
(1.26) From DAQ and N-diethylacetamide the 2,6-bis-(diethylamino-1-ethylene-imino)-anthraquinone having a melting point of 176° C.
(1.27) From DAQ and N-di-n-propylacetamide the 2,6-bis-(di-n-propylamino-1-ethylene-imino)-anthraquinone.
(1.28) From DAQ and N-diisopropylacetamide the 2,6-bis-(diisopropylamino-1-ethylene-imino)-anthraquinone.
(1.29) From DAQ and N-di-n-butylacetamide the 2,6-bis-(di-n-butylamino-1-ethylene-imino)-anthraquinone.
(1.30) From DAQ and N-diisobutylacetamide the 2,6-bis-(diisobutylamino-1-ethylene-imino)-anthraquinone.

(1.31) From DAQ and N-acetylpyrrolidine the 2,6-bis-(pyrrolidino-1-ethylene-imino)-anthraquinone having a melting point of 300° C.

(1.32) From DAQ and N-acetylpiperidine the 2,6-bis-(piperidino-1-ethylene-imino)-anthraquinone.

(1.33) From DAQ and N-acetylmorpholine the 2,6-bis-(morpholino-1-ethylene-imino)-anthraquinone.

(1.34) From DAQ and N-acetylthiomorpholine the 2,6-bis-(thiomorpholino-1-ethylene-imino)-anthraquinone.

(1.35) From 2,6-diamino-anthraquinone (DAQ) and propionamide the 2,6-bis-(amino-1-propylene-imino)-anthraquinone.

(1.36) From DAQ and N-methylpropionamide the 2,6-bis-(methylamino-1-propylene-imino)-anthraquinone.

(1.37) From DAQ and N-ethylpropionamide the 2,6-bis-(ethylamino-1-propylene-imino)-anthraquinone.

(1.38) From DAQ and N-n-propylpropionamide the 2,6-bis-(n-propylamino-1-propylene-imino)-anthraquinone.

(1.39) From DAQ and N-isopropylpropionamide the 2,6-bis-(isopropylamino-1-propylene-imino)-anthraquinone.

(1.40) From DAQ and N-n-butylpropionamide the 2,6-bis-(n-butylamino-1-propylene-imino)-anthraquinone.

(1.41) From DAQ and N-isobutylpropionamide the 2,6-bis-(isobutylamino-1-propylene-imino)-anthraquinone.

(1.42) From DAQ and N-dimethylpropionamide the 2,6-bis-(dimethylamino-1-propylene-imino)-anthraquinone having a melting point of 207° C.

(1.43) From DAQ and N-diethylpropionamide the 2,6-bis-(diethylamino-1-propylene-imino)-anthraquinone having a melting point of 78° C.

(1.44) From DAQ and N-di-n-propylpropionamide the 2,6-bis-(di-n-propylamino-1-propylene-imino)-anthraquinone.

(1.45) From DAQ and N-diisopropylpropionamide the 2,6-bis-(di-isopropylamino-1-propylene-imino)-anthraquinone.

(1.46) From DAQ and N-di-n-butylpropionamide the 2,6-bis-(di-n-butylamino-1-propylene-imino)-anthraquinone.

(1.47) From DAQ and N-diisobutylpropionamide the 2,6-bis-(diisobutylamino-1-propylene-imino)-anthraquinone.

(1.48) From DAQ and N-propionylpyrrolidine the 2,6-bis-(pyrrolidino-1-propylene-imino)-anthraquinone.

(1.49) From DAQ and N-propionylpiperidine the 2,6-bis-(piperidino-1-propylene-imino)-anthraquinone.

(1.50) From DAQ and N-propionylmorpholine the 2,6-bis-(morpholino-1-propylene-imino)-anthraquinone.

(1.51) From DAQ and N-propionylthiomorpholine the 2,6-bis-(thiomorpholine-1-propylene-imino)-anthraquinone.

(1.52) From 2,6-diamino-anthraquinone (DAQ) and pyrrolidone-2 (butyrolactam) 2,6-bis-(pyrrolidone-2-imino)-anthraquinone.

(1.53) From DAQ and 1-methylpyrrolidone-2 the 2,6-bis-(1-methylpyrrolidone-2-imino)-anthraquinone having a melting point of 269° C.

(1.54) From DAQ and 1-ethylpyrrolidone-2 the 2,6-bis(1-ethylpyrrolidone-2-imino)-anthraquinone.

(1.55) From DAQ and 1-propylpyrrolidone-2 the 2,6-bis-(1-propylpyrrlodione-2-imino)-anthraquinone.

(1.56) From DAQ and 1-butylpyrrolidone-2 the 2,6-bis(1-butylpyrrolidone-2-imino)-anthraquinone.

(1.57) From DAQ and piperidone-2 (valerolactam) the 2,6-bis-(piperidone-2-imino)-anthraquinone.

(1.58) From DAQ and 1-methylpiperidone-2 the 2,6-bis-(1-methylpiperidone-2-imino)-anthraquinone having a melting point of 289° C.

(1.59) From DAQ and 1-ethylpiperidone-2 the 2,6-bis-(1-ethylpiperidone-2-imino)-anthraquinone.

(1.60) From DAQ and 1-propylpiperidone-2 the 2,6-bis-(1-propylpiperidone-2-imino)-anthraquinone.

(1.61) From DAQ and 1-butylpiperidone-2 the 2,6-bis-(1-butylpiperidone-2-imino)-anthraquinone.

(1.62) From DAQ and 2-oxohexamethyleneimine (caprolactam) the 2,6-bis-(2-oxohexamethyleneimino-2-imino)-anthraquinone.

(1.63) From DAQ and 1-methyl-2-oxohexamethyleneimine the 2,6-bis-(1-methyl-2-oxohexamethyleneimino-2-imino)-anthraquinone having a melting point of 310° C.

(1.64) From DAQ and 1-ethyl-2-oxohexamethyleneimine the 2,6-bis-(1-ethyl-2-oxohexamethyleneimino-2-imino)-anthraquinone.

(1.65) From DAQ and 1-propyl-2-oxohexamethyleneimine the 2,6-bis-(1-propyl-2-oxohexamethyleneimino-2-imino)-anthraquinone.

(1.66) From DAQ and 1-butyl-2-oxohexamethyleneimine the 2,6-bis-(1-butyl-2-oxohexamethyleneimino-2-imino)-anthraquinone.

EXAMPLE 2 (Method A.a)

2,6-Bis-(1-methylpyrrolidone-2-imino)-anthraquinone 4.8 g of 2,6-diamino-anthraquinone were dissolved in 100 ml of 1-methylpyrrolidone-2-(N-methyl-butyrolactam) and, while stirring at 30°–40° C, 6.1 g of phosphorus oxychloride were added dropwise. The mixture was then heated to 60° C for another hour. On cooling the final product began precipitating as a salt. An addition of 20 ml of methylene chloride completed the precipitation. The salt was suction-filtered, washed with methylene chloride, dried in the air, dissolved in 20 ml of water, 40 ml of methylene chloride were slid beneath this solution, and the base was set free by adding 15 ml of concentrated aqueous ammonia and shaken. The methylene chloride extract was dried with sodium sulfate, evaporated and the residue was recrystallized from toluene. Thus, 6.2 g (78% of the theoretical yield) of 2,6-(1-methylpyrrolidone-2-imino)-anthraquinone were obtained in the form of orange-red crystals having a melting point of 269° C.

In the same manner, the compounds according to Examples 1.52 and 1.54 to 1.66 could be prepared.

EXAMPLE 3 (Method A.b)

2,6-Bis-(dimethylamino-methylene-imino)-anthraquinone 2.4 g of 2,6-diamino-anthraquinone were suspended in 50 ml of pyridine, 4.4 g of dimethylformamide diethyl acetal were added, and the reaction mixture was refluxed for 3 hours (at about 120° C). On cooling the solution, the end product crystallized, it was suction-filtered, washed with acetone and recrystallized from dimethylformamide.

Thus, 2.9 g (83% of the theoretical yield) of 2,6-bis-(dimethylamino-methylene-imino)-anthraquinone were obtained in the form of orange-colored crystals having a melting point of 238° C.

In the same manner, the compounds according to Examples 1.2 to 1.66 could be prepared using corresponding acetals of formula IV as mentioned above.

EXAMPLE 4 (Method B)

2,6-Bis-(morpholino-methylene-imino)-anthraquinone 5 g of 2,6-bis-(trichloroethylene-imino)-anthraquinone were heated to 130° C (reflux) for 2 hours in 100 ml of morpholine without using a diluent. During this operation, split-off chloroform escaped. Excess morpholine was distilled off under reduced pressure, and the residue was recrystallized from dimethylformamide.

Thus, 2,6-(morpholino-methylene-imino)-anthraquinone was obtained, m.p. 300° C.

The 2,6-bis-(trichloroethylene-imino)-anthraquinone used as a starting compound was obtained by reacting 2,6-diamino-anthraquinone with excess anhydrous chloral (trichloro-acdetaldehyde) in polyphosphoric acid in the presence of phosphorus pentoxide for 5 hours at 70° C. In the same manner, there could be obtained the compounds according to Examples 1.1 to 1.51 using corresponding starting material of formulae V and VI as mentioned above.

EXAMPLE 5 (Method C)

2,6-Bis-(1-methyl-pyrrolidone-2-imino)-anthraquinone 48.4 g (0.1 mol) of anthraquinone-2,6-bis-(ω-chlorobutyrylimide chloride) were suspended in 1500 ml of ethylene-glycol dimethyl ether, and gaseous monomethylamine was introduced into this suspension. The reaction was exothermic. After the exothermic reaction had died down, the mixture was heated (under reflux) to 85° C for 1 hour, and the monomethylamine was continued to be introduced. The end product which had crystallized upon cooling was suction-filtered and recrystallized from toluene. Thus, 5.1 g (64% of the theoretical yield) of 2,6-bis-(1-methylpyrrolidone-2-imino)-anthraquinone were obtained, m.p. 286° C. The anthraquinone-2,6-bis-(ω-chlorobutyryl-imide chloride) used as a starting compound was obtained by reacting 2,6-bis-(ω-chlorobutyrylamino)-anthraquinone with phosphorus pentachloride in benzene for 30 minutes at 80° C, and subsequently distilling off the phosphorus oxychloride formed under reduced pressure. The crude product remaining as a residue was further reacted directly. The 2,6-bis-(ω-chlorobutyrylamino)-anthraquinone was obtained by reacting 2,6-diamino-anthraquinone with ω-chlorobutyryl chloride at 110° C without using a diluent; m.p. 300° C.

In the same manner, there could be obtained the compounds according to Examples 1.52 and 1.54 to 1.66 using the corresponding starting compounds of formulae VII and VIII as mentioned above.

EXAMPLE 6 (Method D)

2,6-Bis-(dimethylamino-methylene-imino)-anthraquinone 14.5 g of anthraquinone-2,6-diisocyanate were suspended in 250 ml of dimethylformamide, and the suspension was heated to 160° C (reflux) for 2 hours. During this operation, split-off carbon dioxide escaped. Excess dimethylformamide was distilled off under reduced pressure, and the residue was recrystallized from dimethylformamide. Thus, the 2,6-bis-(dimethylamino-methylene-imino)-anthraquinone was obtained, m.p. 238° C.

The anthraquinone-2,6-diisocyanate used as a starting compound was obtained by reacting 2,6-diamino-anthraquinone with phosgene in boiling xylene or o-dichlorobenzene at 140° C. After the solvent had been distilled off under reduced pressure, the crude product was extracted by means of tetrahydrofuran, evaporated and directly reacted further.

In the same manner, there could be prepared the compounds according to Examples 1.1 to 1.51 using corresponding starting compounds of formula III as mentioned above.

EXAMPLE 7 (Method E)

2,6-Bis-(dimethylamino-methylene-imino)-anthraquinone 10 g of anthraquinone-2,6-bis-carbamic acid chloride were heated to 160° C for 2 hours in 250 ml of dimethylformamide. Excess dimethylformamide was distilled off under reduced pressure, and the residue was recrystallized from diemthylformamide.

Thus, 2,6-bis-(dimethylamino-methylene-imino)-anthraquinone was obtained, m.p. 238° C.

The anthraquinone-2,6-bis-carbamic acid chloride used as a starting compound was obtained by reacting 2,6-diamino-anthraquinone with phosgene in xylene or o-dichlorobenzene at room temperature. The crude product thus obtained was directly reacted further.

In the same manner, there could be obtained the compounds according to Examples 1.1 to 1.51 using the corresponding starting compounds of formula III as mentioned above.

We claim:

1. An anthraquinone-bis-amidine of the formula:

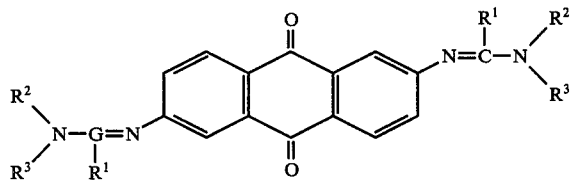

in which $R^1$, $R^2$ and $R^3$ may be identical or different from each other and each represents hydrogen or alkyl of 1 to 4 carbon atoms, as well as an addition salt thereof with a physiologically acceptable acid.

2. A compound as claimed in claim 1, which is 2,6-bis-(dimethylamino-methylene-imino)-anthraquinone.

3. A compound as claimed in claim 1, which is 2,6-bis-(dimethylamino-1-ethylene-imino)-anthraquinone.

4. A compound as claimed in claim 1, which is 2,6-bis-(diethylamino-1-ethylene-imino)-anthraquinone.

5. A compound as claimed in claim 1, which is 2,6-bis-(dimethylamino-1-prcpylene-imino)-anthraquinone.

6. A pharmaceutical composition containing a compound as defined in claim 1 or a salt thereof, in admixture or conjunction with a pharmaceutically acceptable carrier.

7. Method for combating trichomonads which comprises administering to a patient an effective amount of a compound as defined in claim 1 or a salt thereof.

* * * * *